United States Patent [19]

Blume et al.

[11] 4,292,210

[45] Sep. 29, 1981

[54] 1-PHENYL- AND -BENZYL-2,2-DICHLORO-CYCLOPROPANES AS SCENTS

[75] Inventors: Götz Blume; Hans-Otto Müller, both of Holzminden, Fed. Rep. of Germany

[73] Assignee: Bayer Aktiengesellschaft, Leverkusen, Fed. Rep. of Germany

[21] Appl. No.: 656,059

[22] Filed: Feb. 6, 1976

[30] Foreign Application Priority Data

Feb. 22, 1975 [DE] Fed. Rep. of Germany ....... 2507778

[51] Int. Cl.[3] ............................................... A61K 7/46

[52] U.S. Cl. ................................ 252/522 R; 570/182

[58] Field of Search .................. 252/522; 260/648 D, 260/650 R; 570/182

[56] References Cited

U.S. PATENT DOCUMENTS 3,456,023 7/1969 Juveland ........................ 260/650 R

*Primary Examiner*—Curtis R. Davis

*Attorney, Agent, or Firm*—Sprung, Felfe, Horn, Lynch & Kramer

[57] ABSTRACT

1-Phenyl- and -benzyl-2,2-dichloro-cyclopropanes of the formula

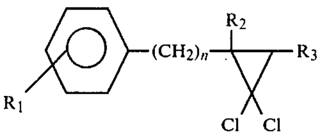

(I)

in which $R_1$ denotes a hydrogen atom or a methyl, ethyl, propyl, methoxy or ethoxy group, $R_2$ and $R_3$ independently of one another represent hydrogen atoms or methyl, ethyl or propyl groups, n is 0 or 1, and the total number of the carbon atoms in the molecule is at most about 15, and preferably at most about 12, are employed as scents in the cosmetic and home hygiene fields.

3 Claims, No Drawings

1-PHENYL- AND -BENZYL-2,2-DICHLORO-CYCLOPROPANES AS SCENTS

The present invention relates to the use of dichlorocyclopropane derivatives as scents.

It has been found that compounds of the general formula

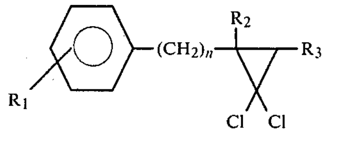

(I)

in which $R_1$ denotes a hydrogen atom or a methyl, ethyl, propyl, methoxy or ethoxy group, $R_2$ and $R_3$ independently of one another represent hydrogen atoms or methyl, ethyl or propyl groups, n is 0 or 1 and the total number of the carbon atoms in the molecule is at most about 15, and preferably at most about 12 are valuable scents. The scents can be used for the preparation of perfume compositions and perfumed products.

A high proportion of the compounds of the formula I are known from scientific publications. However, these publications say nothing about their use. Thus, for example, Chem. Ber. 100, 1858 (1967) and J. Org. Chem. 24, 955 (1969) describe the preparation of 2,2-dichloro-1-phenylcyclopropane and 2,2-dichloro-1-methyl-1-phenyl-cyclopropane, and J. Chem. Soc. 1969, 1024 describes the preparation of 2,2-dichloro-1-methyl-1-phenyl-cyclopropane, 2,2-dichloro-1-methyl-1-p-tolyl-cyclopropane and cis-3,3-dichloro-1,2-dimethyl-1-phenyl-cyclopropane.

The compounds to be used according to the invention can be prepared by reacting compounds of the general formula

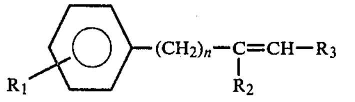

(II)

in which $R_1$, $R_2$, $R_3$ and n have the meaning indicated under the formula I with dichlorocarbene in a manner which is in itself known. The starting compounds of the formula II are known from the literature or can be prepared according to analogous processes. They can be used in technical grades; preferably, however, they are employed in the pure form. Dichlorocarbene is produced in situ, for example from chloroform and a base. As the base it is possible to use, for example, potassium t-butylate [J. Am. Chem. Soc. 76, 6162 (1954)] or ethylene oxide and tetramethylammonium bromide [Tetrahedron Letters (London) 1965, 3585]. Because of the simplicity with which the process can be carried out industrially, and because of the high yields, 50% strength by weight sodium hydroxide solution containing catalytic amounts of triethylbenzylammonium chloride [Tetrahedron Letters (London) 1969, 4659] is preferentially used as the base.

The compounds of the general formula I are distinguished by outstanding scent properties. For some selected compounds, the scent can be represented by the following descriptions:

2,2-Dichloro-1-phenyl-cyclopropane: moist forest soil, geranium, spruce, fresh green.

2,2-Dichloro-1-methyl-1-phenyl-cyclopropane: sharp fresh rose leaf note, earthy, green, rose oxide, diphenylmethane, geranium.

2,2-Dichloro-1-methyl-1-p-tolyl-cyclopropane: mushroom, nut, aniseed, forest soil.

cis-3,3-Dichloro-1,2-dimethyl-1-phenyl-cyclopropane: flowery, dog-rose, fresh timber, vetiver, fruity, gooseberry, wine corks.

trans-3,3-Dichloro-1,2-dimethyl-1-phenyl-cyclopropane: flowery, dog-rose, delicate rose leaf note, vetiver.

2,2-Dichloro-1-ethyl-1-phenyl-cyclopropane: geranium, diphenylmethane, green, flowery.

3,3-Dichloro-1-ethyl-2-phenyl-cyclopropane: fruity, mint-like, plum, flowery.

trans-3,3-Dichloro-1-methyl-2-benzyl-cyclopropane: animal, naphthalene, dimethylbenzylcarbinol, jasmine.

2,2-Dichloro-1-o-tolyl-cyclopropane: herbaceous, Roman camomile, somewhat woody, α-phellandrene.

2,2-Dichloro-1-methyl-3-p-methoxy-phenyl-cyclopropane: herbaceous, fennel-like, aniseed, woody.

The compounds to be used according to the invention possess, in addition to their excellent scent properties, excellent cling and excellent stability both in an acid and an alkaline medium.

The present invention provides a perfume composition containing a compound of the formula (I) in admixture with one or more other perfume ingredients.

The perfume compositions of the invention may contain, in addition to the compound of the formula (I) any other perfume ingredient or combination of ingredients known to perfume chemists and selected and admixed in such quantities that the resultant odour is of the desired fragrance, for example alcohols, aldehydes, esters, ketones and hydrocarbons.

The compounds of the formula (I) may also be used alone in perfumed compositions and the invention therefore also includes a perfumed composition comprising a compound of the formula (I) in admixture with a solid or liquefied gaseous diluent or carrier, or a liquid diluent or carrier other than a liquid solvent of molecular weight less than 200 (preferably less than 300) except in the presence of a surface-active agent. Specific examples of suitable diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

The compounds of the formula (I) are safe both dermatologically and toxicologically and are useful in the manufacture of cosmetic, toiletry and cleansing preparations. The invention therefore specifically provides a method of altering the odour of a cosmetic, toiletry or cleansing preparation comprising incorporating therein a compound of the formula (I).

The invention also includes a perfumed cosmetic, toiletry or cleansing preparation comprising, as an active perfume ingredient, a compound of the formula (I).

The preparations into which the compounds of the formula (I) may be in the form of ointments, gels, pastes, creams, sprays (including aerosols), lotions, suspensions, solutions and emulsions in aqueous or non-aqueous diluents, granules or powders. The preparations of the invention therefore include all the finished products in the cosmetics, fine perfumery, aerosol and washing agent fields, and especially in the field of products of the chemical industry, for example detergents, hair preparations, foam baths, bath salts, dishwashing agents, agents for use in dishwashing machines, shampoos, softener rinses for laundry, washing powders, soaps, antiperspirants, powders, creams, shaving lotions, after shave lotions, air fresheners, WC-cleaner, air freshener sprays, antiperspirant sprays, deodorant sprays, body sprays, insecticide sprays and antisunburn agents.

In these preparations, the compounds to be used according to the invention are employed, for example, in amounts of 0.001 to 10, preferably 0.01 to 10, percent by weight, relative to the finished preparation.

The compounds to be used according to the invention can be employed by themselves or mixed with one another or in combination with other scents.

Of the compounds to be used according to the invention, 2,2-dichloro-1-methyl-1-phenyl-cyclopropane is preferred because of its particularly attractive suggestion of roses and geranium. This substance offers very many possible applications because of its numerous scent suggestions, which in themselves make the substance produce the effect of a composition.

Preparation of the dichlorocyclopropane derivatives used in the examples:

1. 2,2-Dichloro-1-methyl-1-phenyl-cyclopropane

A solution of 3 g of triethylbenzylammonium chloride in 500 g of chloroform is added over the course of 5 minutes to 800 g of 50% strength by weight sodium hydroxide solution in a 2 l stirred apparatus equipped with a dropping funnel and internal thermometer, at 50° C., whilst cooling and stirring slowly. A solution of 345 g of α-methylstyrene in 300 g of chloroform is added dropwise over the course of 45 minutes to the preceding mixture with vigorous stirring and cooling at 50° C. After stirring for a further 4 hours at 50° C., the reaction mixture is cooled to 20° C. and neutralised with concentrated hydrochloric acid at 10°-20° C., whilst cooling. It is then diluted with 2 l of water and the organic phase is separated off. The aqueous phase is extracted with 100 g of chloroform. The combined organic phases are washed with 250 g of water and 100 g of 10% strength by weight sodium carbonate solution. The solvent is then distilled off and the residue is subjected to fractional distillation. This gives 561 g=92.9% of theory of 2,2-dichloro-1-methyl-1-phenyl-cyclopropane of boiling point 116°-117° C./17 mm.

If instead of α-methylstyrene the equivalent amount of one of the aralkenes listed in the table which follows was employed, the dichlorocyclopropane derivatives also indicated in the table were obtained.

TABLE

| Aralkene | Dichlorocyclopropane derivative | Boiling point (°C./mm Hg) | Yield (%) |
|---|---|---|---|
| 1-Phenyl-butene-1 | 3,3-Dichloro-1-ethyl-2-phenylcyclopropane (mixture of 86% trans- and 14% cis-compound) | 95–97°/2 | 83 |
| 1-Methyl-1-phenylpropene-1 (trans-compound) | 3,3-Dichloro-1,2-dimethyl-1-phenylcyclopropane (trans-compound) | 74–76°/0.7 | 79 |
| 1-Methyl-1-phenylpropene-1 (cis-compound) | 3,3-Dichloro-1,2-dimethyl-1-phenylcyclopropane (cis-compound) | 73–75°/0.6 | 78 |
| 2-p-Tolyl-propene-1 | 2,2-Dichloro-1-methyl-1-p-tolylcyclopropane | 94–95°/2 | 89 |
| 1-Phenyl-butene-2 (trans-compound) | 3,3-Dichloro-1-methyl-2-benzylcyclopropane (trans-compound) | 84–85°/0.6 | 82 |
| 2-Methyl-styrene | 2,2-Dichloro-1-o-tolylcyclopropane | 80–82°/1.5 | 75 |
| α-Ethyl-styrene | 2,2-Dichloro-1-ethyl-1-phenylcyclopropane | 70–73°/0.6 | 87 |
| 1-(p-Methoxyphenyl)-propene-1 (trans-compound) | 2,2-Dichloro-1-methyl-3-(p-methoxyphenyl)-cyclopropane (trans-compound) | 105–107°/0.5 | 86 |

II. 2,2-Dichloro-1-phenyl-cyclopropane (a) 31.2 g of styrene, 40 g of chloroform, 1 g of tetraethylammonium bromide, 0.2 g of hydroquinone and 22 g of ethylene oxide are cooled and mixed, and the mixture is divided between two cooled bomb tubes. These are sealed by fusing, and heated, in a steel jacket, to 160° C. for 7.5 hours. After cooling, the bomb tubes are opened and the contents are combined. 100 g of hexane are added to the reaction mixture and the whole is washed 3 times each with 100 g of water. The organic phase is freed from the solvent and subjected to fractional distillation. Yield: 31.8 g=57% of theory of 2,2-dichloro-1-phenyl-cyclopropane of boiling point 103°-105° C./14 mmm.

(b) 312 g of styrene are reacted with chloroform as described in (I). After a post-reaction time of 5 hours, fractional distillation gives 45 g of styrene and 444 g of 2,2-dichloro-1-phenyl-cyclopropane of boiling point 103°-104° C./11 mm. This corresponds to 79.2% of theory or 93% based on styrene converted.

(c) 30 g of potassium t-butylate are initially introduced, under nitrogen, into a 500 ml stirred apparatus fitted with an internal thermometer and dropping funnel, and are cooled to −5° C. 156 g of styrene are added thereto, followed by 30 g of freshly distilled, dry chloroform added dropwise over the course of 1 hour at −5° C., whilst stirring. The mixture is stirred for a further 3 hours at −5° C. and is then left to stand for 20 hours at 10° C. It is warmed to room temperature, 200 g of water are added, and the whole is neutralised with 10% strength by weight hydrochloric acid. The organic layer is separated off and the aqueous phase is extracted with 100 g of hexane. The combined organic phases are washed with 100 g of water and dried with sodium sulphate. Distillation gives 2,2-dichloro-1-phenylcyclopropane of boiling point 101°-105° C./14 mm. Yield 35 g=75% of theory.

EXAMPLE 1

Preparation of a perfume oil

The following recipe is given as an example of the preparation of a perfume oil (composition in parts by weight): 5 pelargonaldehyde, 10% strength in diethyl phthalate; 15 undecylenaldehyde, 10% strength in diethyl phthalate; 10 laurylaldehyde, 10% strength in diethyl phthalate; 10 methylnonylacetaldehyde, 10% strength in diethyl phthalate; 5 γ-undecalactone, 10% strength in diethyl phthalate; 10 linalool; 10 cyclamenaldehyde; 5 anisaldehyde; 5 cananga oil; 10 isoamyl salicylate; 5 isoeugenol; 10 ionone; 150 benzyl acetate; 30 α-amylcinnamaldehyde; 10 indole, 10% strength in diethyl phthalate; 5 civet extract, 10% strength in diethyl phthalate; 100 terpineol; 150 phenylethyl alcohol; 100 geraniol; 5 Bourbon geranium oil; 30 citronellol; 15 Florida cedarwood oil; 5 guaiacum oil; 20 cinnamyl alcohol; 10 coumarin; 10 Ambrette musk; 10 musk xylene (?); 250 trans-3,3-dichloro-1,2-dimethyl-1-phenyl-cyclopropane; total 1,000.

The addition of 250 parts of trans-3,3-dichloro-1,2-dimethyl-1-phenyl-cyclopropane results in a flowery, fresh effect which rounds off the scent complex and makes it lighter and more radiant.

EXAMPLE 2

Preparation of a perfume oil

The following recipe is given as an example of the preparation of a perfume oil (composition in parts by weight): 15 methylnonylacetaldehyde; 50 p-tert.-butyl-α-methylhydrocinnamaldehyde; 20 dihydromyrcenol; 70 Spanish lavender oil; 250 isobornyl acetate; 50 elemi resin; 10 olibanum resin; 15 galbanum resin; 10 concrete lavandine; 10 Dalmatian sage oil; 10 Bourbon geranium oil; 30 East Indian sandalwood oil; 30 Florida cedarwood oil; 20 α-hexylcinnamaldehyde; 10 6-acetyl-1,1,3,4,4,6-hexamethyl-tetrahydronaphthalene; 100 diethyl phthalate; 300 2,2-dichloro-1-methyl-1-phenyl-cyclopropane; total 1,000.

As a result of the addition of 300 parts of 2,2-dichloro-1-methyl-1-phenyl-cyclopropane the composition acquires greater fullness and a tingling freshness. The oil has a cosmetic effect as a result of the additive, and arouses a picture of cleanness and freshness.

EXAMPLE 3

Preparation of a perfume oil

The following recipe is given as an example of the preparation of a perfume oil (composition in parts by weight): 100 benzyl acetate; 100 citronellol; 100 phenylethyl alcohol; 150 terpineol; 50 p-tert.-butyl-α-methylhydrocinnamaldehyde; 50 isoamyl salicylate; 50 ionone; 50 anisaldehyde; 25 lavandine oil; 20 dihydromyrcenol; 20 cinnamyl alcohol; 15 α-amylcinnamaldehyde; 10 γ-undecalactone; 10 phenylethyl isoamyl ether; 5 cananga oil; 5 laurylaldehyde, 10% strength in diethyl phthalate; 5 Bourbon geranium oil; 5 coumarin; 10 6-acetyl-1,1,3,4,4,6-hexamethyltetrahydronaphthalene; 20 α-trichloromethyl-benzyl alcohol acetate; 200 3,3-Dichloro-1-ethyl-2-phenyl-cyclopropane: total 1,000.

As a result of the addition of 200 parts of 3,3-dichloro-1-ethyl-2-phenyl-cyclopropane the perfume oil gives a fresher, more delicate and rounded impression.

EXAMPLE 4

Preparation of a perfume oil

The following recipe is given as an example of the preparation of a perfume oil (composition in parts by weight): 300 phenylethyl alcohol; 250 dihydrocitronellol; 80 α-trichloromethyl-benzyl alcohol acetate; 5 6-acetyl-1,1,3,4,4,6-hexamethyl-tetrahydronaphthalene; 5 phenylacetic acid ethyl ester; 5 heptinecarboxylic acid methyl ester, 10% strength in diethyl phthalate; 5 γ-undecalactone, 10% strength in diethyl phthalate; 350 2,2-dichloro-1-methyl-1-phenylcyclopropane: total 1,000.

As a result of the addition of 350 parts of 2,2-dichloro-1-methyl-1-phenyl-cyclopropane a rose leaf effect is produced, which only now completes the scent of red rose. Furthermore, the additive produces a more effervescent and natural effect.

EXAMPLE 5

Preparation of a perfume oil

The following recipe is given as an example of the preparation of a perfume oil (composition in parts by weight): 70 2,6-dimethylheptanol-2; 30 dihydrocitronellol; 150 terpineol; 5 phenylethyl isoamyl ether; 5 2-heptylcyclopentanone; 100 phenylethyl alcohol; 30 nonanediol-1,3-diacetate; 5 p-methoxy-acetophenone; 3 hydroquinone dimethyl ether; 2 6-acetyl-1,1,3,4,4,6-hexamethyl-tetrahydronaphthalene; 600 2,2-dichloro-1-methyl-1-phenyl-cyclopropane: total 1,000.

The perfume oil is a flowery complex of scents with a fruity suggestion. It is reminiscent of the scent of roses, lilac and jasmine.

EXAMPLE 6

Preparation of an air freshener spray

An air freshener spray perfumed with the perfume oil from Example 3 is prepared, for example, as follows: an aerosol can is filled with a mixture of 19.8 g of isopropyl alcohol and 0.2 g of perfume oil from Example 3. After sealing the aerosol can, 80 g of difluorodichloromethane are injected through the valve.

The resulting air freshener spray has a full, rounded scent of roses of high intensity and fullness of scent.

EXAMPLE 7

Preparation of a toilet cleaner

A granular acid toilet cleaner perfumed with the perfume oil from Example 3 consists of the following constituents (composition in parts by weight): 85.6 sodium bisulphate; 8.0 sodium bicarbonate; 2.0 sodium carbonate; 1.0 powdered silicon dioxide; 3.0 sodium salt of the sulphosuccinic acid half-ester of lauric acid monoethanolamide; 0.2 perfume oil from Example 3; 0.2 paraffin oil: total 100.0.

The toilet cleaner is prepared as follows: the perfume oil and paraffin oil are worked into a mixture of silicon dioxide, sodium bicarbonate, sodium carbonate and the sodium salt of the sulphosuccinic acid half-ester of lauric acid monoethanolamide. This premix is mixed with the sodium bisulphate.

The toilet cleaner has a very intense, radiant scent of roses which arouses the impression of cleanness and freshness.

EXAMPLE 8

Preparation of an acid toilet cleaner

An acid toilet cleaner (for dissolving urine scale), perfumed with the perfume oil from Example 3, consists of the following constituents (composition in parts by weight): 12.0 amidosulphonic acid; 3.0 nonylphenol polyglycol ether; 1.0 perfume oil from Example 3; 84.0 water: total 100.0.

The acid toilet cleaner is prepared as follows: the nonylphenol polyglycol ether and the perfume oil from Example 15 are mixed and dissolved in slightly warmed water. The amidosulphonic acid is then dissolved therein.

The resulting agent for dissolving urine scale has the full scent of red roses. The scent has a radiant, clean and fresh effect.

EXAMPLE 9

Preparation of a scouring powder with active oxygen

A scouring powder with active oxygen, perfumed with the perfume oil from Example 1, consists of the following constituents (composition in parts by weight): 4.0 sodium dodecylbenzenesulphonate; 2.0 sodium carbonate; 1.0 sodium perborate; 0.2 perfume oil from Example 1; 92.8 calcite powder of approximate diameter 20–40$\mu$: total 100.0.

The scouring powder with active oxygen is prepared as follows: the perfume oil is mixed with the sodium dodecylbenzenesulphonate, this mixture is worked into a powder with 50% of the calcite powder, to give a premix, and the remaining raw materials are then added.

The resulting scouring powder has a fresh and natural smell and its scent is reminiscent of forests and sea-surf.

EXAMPLE 10

Preparation of a softener rinse for laundry

A softener rinse for laundry, perfumed with perfume oil from Example 2, consists of the following constituents (composition in parts by weight): 5.0 dimethyl-distearylammonium chloride; 2.0 fatty acid polyglycol ester; 1.0 dimethyl-$C_{14}$–$C_{16}$-alkyl-benzyl-ammonium chloride; 0.2 cationic optical brightener; 0.1 anti-foaming agent solution, 10% strength by weight in water; 1.0 dyestuff solution, 0.1% strength by weight in water; 0.4 perfume oil from Example 2; 90.3 water: total 100.0.

The softener rinse for laundry is prepared as follows: 50% of the water required is heated to 80°–85° C. and the dimethyl-distearyl-ammonium chloride is added. The mixture is slowly cooled to 50°–55° C. with vigorous stirring and the fatty acid polyglycol ester is added. After emulsification, the remaining raw materials and the remaining cold water are added so slowly as to avoid spontaneous cooling.

The softener rinse for laundry which is obtained has an attractive, full, cosmetic-like odour of a flowery type.

EXAMPLE 11

Preparation of a heavy duty detergent

An unperfumed heavy duty detergent is prepared from the following constituents (composition in parts by weight): 9.00 sodium dodecylbenzenesulphonate; 2.00 ethylene oxide/propylene oxide condensate; 6.00 coconut oil-tallow soap; 3.00 sodium toluenesulphonate; 2.20 fatty alcohol polyglycol ether (1 mol of oleyl alcohol + 12 mols of ethylene oxide); 1.15 carboxymethylcellulose; 26.00 sodium tripolyphosphate; 12.00 tetrapotassium pyrophosphate; 3.00 trisodium phosphate; 4.00 magnesium silicate; 4.00 sodium carbonate; 12.06 sodium sulphate; 0.44 optical brightener; 15.00 sodium perborate: total: 99.85.

The addition of 0.15 part by weight of the perfume oil from Example 1 produces a fresh, spicy odour of the heavy duty detergent, arousing the impression of fresh, clean air and sea-surf.

EXAMPLE 12

Preparation of a dishwashing agent

A pulverulent dishwashing agent, perfumed with the perfume oil from Example 4, for dishwashers, consists of the following constituents (composition in parts by weight): 54.00 sodium metasilicate; 30.00 sodium tripolyphosphate; 6.00 trisodium phosphate; 6.60 sodium carbonate; 2.20 ethylene oxide/propylene oxide condensate; 1.00 sodium dichloroisocyanurate; 0.20 perfume oil from Example 4: total 100.00.

The pulverulent dishwashing agent for dishwashers is prepared as follows: the ethylene oxide/propylene oxide condensate is mixed with the perfume oil from Example 4 and the mixture is worked into the sodium polyphosphate. Thereafter the other raw materials are admixed.

The dishwashing agent for dishwashers has an attractive fresh scent of blossom, which in all stages masks the intrinsic scent of the dishwashing agent for dishwashers very well.

EXAMPLE 13

Preparation of a soap 100 g of soap chips are milled with 1 g of perfume oil from Example 1, 1 g of titanium dioxide and 1 g of a 1% strength by weight dyestuff solution in water until a soap mass of practically homogeneous composition is obtained. After homogenisation, the soap mass is pressed to give a cake of soap.

The resulting cake of soap has a spicy fresh smell. The scent is reminiscent of the clean, fresh air at the seaside and in forests.

EXAMPLE 14

Preparation of a soap 100 g of soap chips are milled with 1 g of perfume oil from Example 1, 1 g of titanium dioxide and 1 g of a 1% strength by weight dyestuff solution in water until a soap mass of practically homogeneous composition is obtained. The resulting soap mass is pressed to give a cake of soap.

The cake of soap has a scent resembling a bouquet of flowers, with an extract-like edge which in total produces a very pleasant and cosmetic effect.

It will be appreciated that the instant specification and examples are set forth by way of illustration and not limitation, and that various modifications and changes may be made without departing from the spirit and scope of the present invention.

What is claimed is:

1. A scented composition comprising a perfume as carrier and about 0.01 to 10 percent by weight of at least one compound of the formula

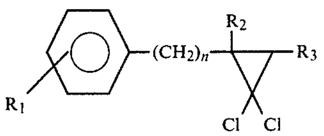

in which $R_1$ denotes a hydrogen atom or a methyl, ethyl, propyl, methoxy or ethoxy group, $R_2$ and $R_3$ independently of one another represent hydrogen atoms or methyl, ethyl or propyl groups, n is 0 or 1 and the total number of carbon atoms in the molecule is at most 12.

2. A scented composition according to claim 1, wherein said compound is 2,2-dichloro-1-methyl-1-phenyl-cyclopropane.

3. A perfume according to claim 1, containing at least one additional ingredient selected from the group consisting of alcohols, aldehydes, esters, ketones and hydrocarbons.

* * * * *

UNITED STATES PATENT AND TRADEMARK OFFICE
CERTIFICATE OF CORRECTION

PATENT NO. : 4,292,210

DATED : Sep. 29, 1981

INVENTOR(S) : Götz Blume et al

It is certified that error appears in the above-identified patent and that said Letters Patent are hereby corrected as shown below:

| | |
|---|---|
| Title Page Assignee | Delete "Bayer Aktiengesellschaft, Leverkusen" and insert --Harmann & Reimer GmbH, Holzminden--. |

Signed and Sealed this

*Eleventh* Day of *May 1982*

[SEAL]

*Attest:*

GERALD J. MOSSINGHOFF

*Attesting Officer* *Commissioner of Patents and Trademarks*